United States Patent
Swaminathan

(10) Patent No.: US 9,871,777 B2
(45) Date of Patent: Jan. 16, 2018

(54) WEB-BASED DATA AND INSTRUMENT MANAGEMENT SOLUTION

(71) Applicant: Siemens Healthcare Diagnostics Inc., Tarrytown, NY (US)

(72) Inventor: Mahalingam Swaminathan, Stoughton, MA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 0 days.

(21) Appl. No.: 14/362,697

(22) PCT Filed: Dec. 4, 2012

(86) PCT No.: PCT/US2012/067723
§ 371 (c)(1),
(2) Date: Jun. 4, 2014

(87) PCT Pub. No.: WO2013/085884
PCT Pub. Date: Jun. 13, 2013

(65) Prior Publication Data
US 2014/0359752 A1    Dec. 4, 2014

Related U.S. Application Data

(60) Provisional application No. 61/567,885, filed on Dec. 7, 2011.

(51) Int. Cl.
*G06F 21/44* (2013.01)
*H04L 29/06* (2006.01)
(Continued)

(52) U.S. Cl.
CPC .............. *H04L 63/08* (2013.01); *G06F 17/30* (2013.01); *G06F 21/44* (2013.01); *G06Q 10/06* (2013.01);
(Continued)

(58) Field of Classification Search
CPC ....................................................... G06F 21/44
(Continued)

(56) References Cited

U.S. PATENT DOCUMENTS 6,320,380 B1 * 11/2001 Wu et al. .................... 324/309
6,415,048 B1 *  7/2002 Schneider .................... 382/131
(Continued)

FOREIGN PATENT DOCUMENTS

WO    2006052215 A1    5/2006

OTHER PUBLICATIONS

International Search Report and Written Opinion of International Application No. PCT/US2012/067723 dated Apr. 9, 2013.
(Continued)

*Primary Examiner* — William Powers
(74) *Attorney, Agent, or Firm* — Kyle D. Petaja

(57) ABSTRACT

A data and instrument management and interface system comprises a web server hosted on an intranet network having a wireless range. The web server has a processor, and a non-transitory computer memory coupled with the processor and storing processor executable code. The web server can communicate over the intranet network with a web browser running on a handheld user device located within the wireless range of the intranet network, and with an instrument. The processor executable code causes the processor to: receive a first wireless signal over the intranet network, the first wireless signal transmitted by the web browser and indicative of request for data for the instrument; authenticate the handheld user device and a user of the web browser; and transmit a second wireless signal to the web browser indicative of data for the instrument responsive to the handheld user device and the user being authenticated.

13 Claims, 5 Drawing Sheets

(51) Int. Cl.
*G06F 17/30* (2006.01)
*H04L 29/08* (2006.01)
*G06Q 10/06* (2012.01)
*G06Q 10/10* (2012.01)
*G06Q 50/22* (2012.01)
*H04W 12/06* (2009.01)
*G06F 19/00* (2011.01)

(52) U.S. Cl.
CPC ............ *G06Q 10/10* (2013.01); *G06Q 50/22* (2013.01); *H04L 29/06* (2013.01); *H04L 67/025* (2013.01); *H04L 67/12* (2013.01); *H04L 67/125* (2013.01); *H04W 12/06* (2013.01); *G06F 19/327* (2013.01); *G06F 2221/2111* (2013.01)

(58) Field of Classification Search
USPC .......................................................... 726/16
See application file for complete search history.

(56) References Cited

U.S. PATENT DOCUMENTS

| | | | |
|---|---|---|---|
| 6,460,141 B1* | 10/2002 | Olden | ................... G06F 21/604 726/12 |
| 6,732,105 B1* | 5/2004 | Watson et al. | |
| 7,184,999 B1* | 2/2007 | Watson et al. | ................ 707/770 |
| 2003/0154147 A1 | 8/2003 | Parry | |
| 2007/0162860 A1* | 7/2007 | Muralidharan et al. | ...... 715/736 |
| 2009/0074184 A1 | 3/2009 | Baum et al. | |
| 2010/0023865 A1 | 1/2010 | Fulker et al. | |

OTHER PUBLICATIONS

European Search Report and Opinion of European Application No. EP 12856394 dated Jul. 2, 2015.

* cited by examiner

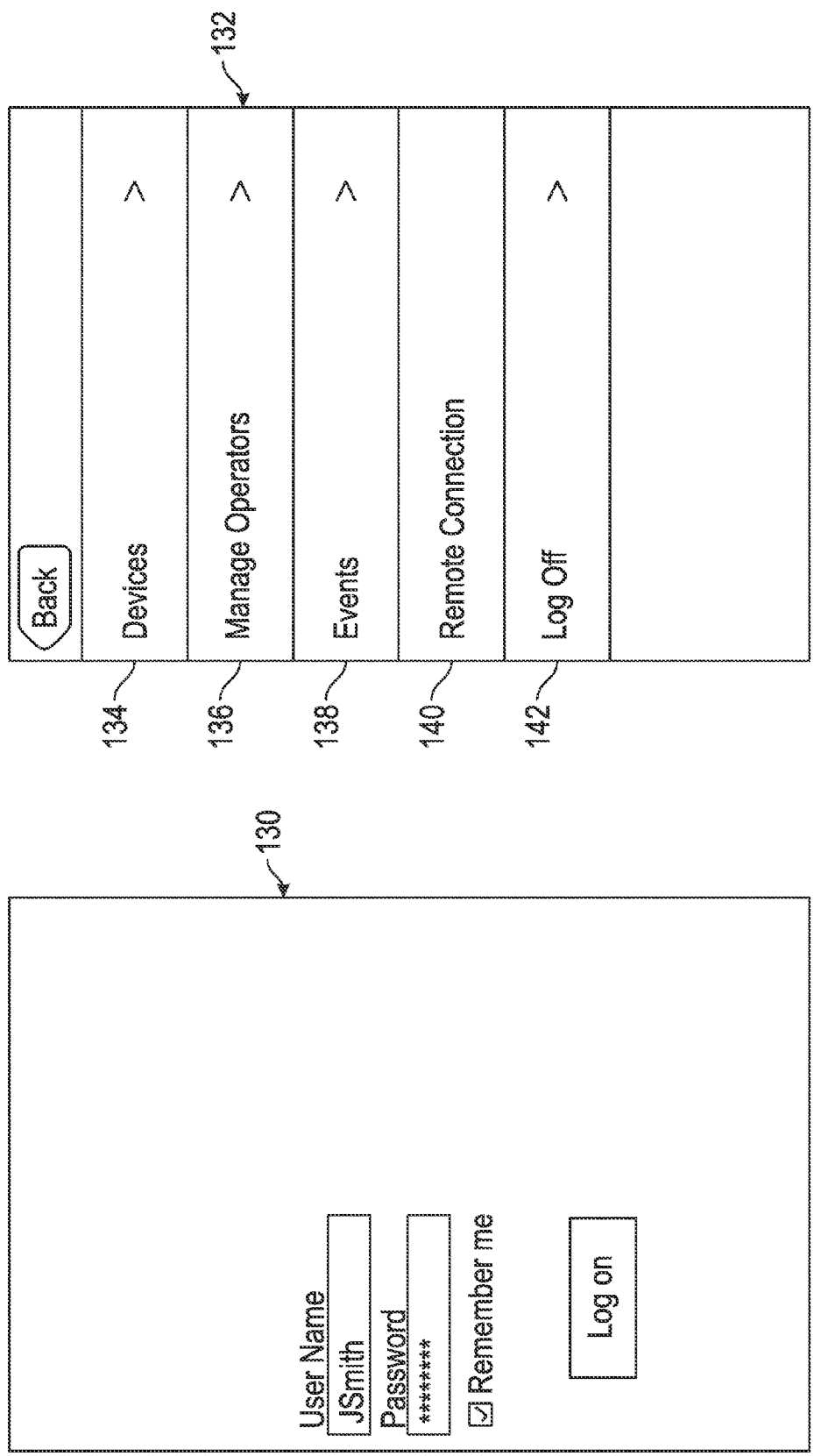

Device Details — 146

Back

Device Name: DCA WE1
Model Type: Diabetes
Software Version: 3.0
Device Location: POCC
Connection Status: Offline
Last Patient:
Last QC:

Device Link — 148 | Video Log — 150

FIG. 5

Device List — 144

Back

| Location | Device Name | Conn. Status | Dev. Status | |
|---|---|---|---|---|
| POCC | DCA WE1 | ◉ | ○ | > |
| POCC | DCA WE2 | ◉ | ○ | > |

FIG. 4

WEB-BASED DATA AND INSTRUMENT MANAGEMENT SOLUTION

INCORPORATION BY REFERENCE

The entirety of U.S. Provisional Application Ser. No. 61/567,885, filed on Dec. 7, 2011, is hereby expressly incorporated herein by reference.

BACKGROUND

1. Field of Inventive Concepts

The inventive concepts disclosed herein generally relate to the diagnostic healthcare industry, and more particularly, but not by way of limitation, to web-based data and instrument management and interface systems and methods.

2. Brief Description of Related Art

Data management systems in the automated in vitro diagnostic healthcare industry are known and provide a solution to the growing need of point-of care coordinators (POCCs) and laboratory managers for centralized management and standardized testing procedures for their analyzers or other equipment, instruments, and devices. Analyzers include instruments for the detection and determination of urine chemistries and sediment, blood gases, electrolytes and metabolites, blood glucose, HbA1c, as well as numerous other analytes found in body fluids. Analyzers have recently come to include functionality such as operator and quality control lock-out, as well as communication choices of wireless or hard-wired networks and HL7 or POCT1-A2 protocols.

These connectivity enhancements are expected to increase the need for analyzers and other equipment to be managed by point of care (POC) information technology systems. For example, the POCT1-A2 POC connectivity standard, as implemented in the CLINITEK Status® Connect System (available from Siemens Healthcare Diagnostics Inc.), supports operator list downloads, remote device configuration, and remote control, in addition to patient and quality control results reporting. The RAPIDComm® v3.0 data management system works with the CLINITEK Status® Connect System's communication protocols to offer automatic operator list updates and downloads, triggered by changes in operator credentials and recertification updates.

Data management solutions for point of care instruments are traditionally only available with wired connections using laptops and are restricted to the physical location where the data management software is installed. Users are still using wired computers and workstations which need data management software installed on them. Another issue with prior art data management systems in medical institutions is that the institutions have many different ways of achieving connectivity; the right point-of-care solutions would accommodate these different connectivity scenarios.

SUMMARY

The inventive concepts disclosed herein allow users to manage patient and instrument data across point of care instruments through a handheld or mobile wireless device having a web browser. As opposed to creating device specific applications for each handheld or mobile device, a web browser application reduces costs in terms of development of custom applications for each device and makes the user experience common across different devices.

One unique aspect of some exemplary embodiments of a web-based application according to the inventive concepts disclosed herein is that the web-based application is targeted for handheld devices which are wireless. Wireless connectivity presents a challenge in terms of security, especially when handling healthcare information. The inventive concepts disclosed herein, in one embodiment, include a web server hosted within the hospital or other healthcare institution's intranet, which makes this application available only within the hospital or institution, to enhance security, for example.

One exemplary embodiment of the inventive concepts disclosed herein includes a web-based data and instrument management and interface system including a web server that is hosted in a central location and has clients access this web server using the web application. In one embodiment, the web server is hosted within the hospital's intranet. A data and instrument management and interface system such as Siemens Healthcare Diagnostics' RAPIDComm® system, for example, may be operably connected to the hospital's intranet and/or to the web server. Consequently, both the data and instrument management and interface system and the web server are within the same hospital's internal network, and may communicate with one another via the hospital's internal network or intranet.

Another advantageous feature for data management solution systems is the ability to capture screenshots of the medical instruments being monitored as a method of providing technical support to a customer or a user operating the medical instrument (e.g., an analyzer). In one exemplary embodiment of the inventive concepts disclosed herein, a medical instrument coupled with a data and instrument management and interface system, such as the RapidComm® system, can be set to capture screenshots of the medical instrument and send the captured screenshots to a remote technician (e.g., technical support) utilizing the remote connection functionality of the system. Remote connection can be used to capture screenshots of the medical instrument and convert the captured screenshots into a video. The video can then be sent or otherwise made available to customer support if a technical issue is to be resolved. The capture can be initiated via a web-based application or a web browser running on a handheld wireless device connected to a data and instrument management and interface system as described herein.

In one aspect, the inventive concepts disclosed herein are directed to a data and instrument management and interface system comprising a web server hosted on an intranet network having a wireless range, the web server having a processor capable of executing processor executable code, and one or more non-transitory computer memory operably coupled with the processor and storing processor executable code. The web server is configured to communicate over the intranet network with a web browser running on a handheld user device located within the wireless range of the intranet network and to communicate with one or more instrument coupled with the web server. The processor executable code, when executed by the processor, causes the processor to: (1) receive a first wireless signal over the intranet network, the first wireless signal transmitted by the web browser running on the handheld user device from within the wireless range of the intranet network and indicative of a request for data for the one or more instrument; (2) authenticate the handheld user device located within the wireless range of the intranet network; (3) authenticate a user of the web browser running on the handheld user device; and (4) transmit a second wireless signal over the intranet network to the web browser running on the handheld user device responsive to the handheld user device and the user being authenticated, the second wireless signal indicative of data for the one or more instrument. The handheld user device may be authenticated by accessing a list of one or more predetermined handheld used devices.

The processor executable code, when executed by the processor, may further cause the processor to: (a) receive a third wireless signal over the intranet network, the third wireless signal indicative of a request for a remote connection to the one or more instrument by the web browser; and (b) transmit a fourth wireless signal over the intranet network to the web browser, the fourth wireless signal indicative of the remote connection to the one or more instrument.

The processor executable code, when executed by the processor may further cause the processor to: (c) receive a fifth signal over the intranet network, the fifth signal indicative of a command to initiate capture of one or more screenshots of a screen of the one or more instrument from the web browser; (d) receive a sixth signal from the one or more instrument, the sixth signal indicative of one or more screenshots of the screen of the one or more instrument; (e) capture one or more screenshots of the screen of the one or more instrument; and (f) transmit a seventh signal indicative of the one or more captured screenshots. The seventh signal may be transmitted to a technician over the intranet network. The seventh signal may be transmitted to the web browser over the intranet network. The one or more instrument may be a point-of-care instrument, an analyzer, a medical instrument, a laboratory instrument in a laboratory setting, an industrial machine, an industrial device, or an industrial robot, and combinations thereof.

In another aspect, the inventive concepts disclosed herein are directed to a data and instrument management and interface system comprising a web server hosted on an intranet network, the web server having a processor capable of executing processor executable code, and one or more non-transitory computer memory operably coupled with the processor and storing processor executable code. The web server is configured to communicate over the intranet network with a web browser running on a handheld user device coupled with the intranet network and to communicate with one or more instrument coupled with the web server. The processor executable code, when executed by the processor, causes the processor to: (1) receive a first signal over the intranet network indicative of a request from the web browser running on the handheld user device for a remote connection with the one or more instrument; (2) authenticate that the handheld user device is coupled with the intranet network; (3) authenticate a user of the web browser running on the handheld user device; and (4) transmit a second signal over the intranet network to the web browser running on the handheld user device responsive to authenticating the handheld user device and the user, the second signal indicative of the remote connection with the one or more instrument.

The processor executable code, when executed by the processor, may further cause the processor to: (a) receive a fifth signal over the intranet network, the fifth signal indicative of a command to initiate capture of one or more screenshots of a screen of the one or more instrument from the web browser; (b) receive a sixth signal from the one or more instrument, the sixth signal indicative of one or more screenshots of the screen of the one or more instrument; (c) capture one or more screenshots of the screen of the one or more instrument; and (d) transmit a seventh signal indicative of the one or more captured screenshots. The seventh signal may be transmitted to a remote technician over the intranet network and/or may be transmitted to the web browser over the intranet network.

The one or more instrument may be a point-of-care instrument, an analyzer, a medical instrument, a laboratory instrument in a laboratory setting, an industrial machine, an industrial device, or an industrial robot, and combinations thereof.

In yet another aspect, the inventive concepts disclosed herein are directed to a data and instrument management and interface system comprising a web server hosted on an intranet network, the web server having a processor capable of executing processor executable code, and one or more non-transitory computer memory operably coupled with the processor and storing processor executable code. The web server is configured to communicate over the intranet network with a web browser running on a handheld user device coupled with the intranet network, and to communicate with one or more instrument having a screen and being coupled with the web server. The processor executable code, when executed by the processor, causes the processor to: (1) receive a first signal over the intranet network indicative of a command to initiate capture of one or more screenshots of the screen of the one or more instrument from the web browser running on the handheld user device; (2) authenticate the handheld user device; (3) authenticate a user of the web browser running on the handheld user device; (4) receive a second signal from the one or more instrument, the second signal indicative of one or more screenshots of the screen of the one or more instrument; (5) capture one or more screenshots of the screen of the one or more instrument; and (6) transmit a third signal over the intranet network to the web browser indicative of the one or more captured screenshots.

The processor executable code, when executed by the processor, may further cause the processor to transmit a fourth signal over the intranet network to a remote technician, the fourth signal indicative of the one or more captured screenshots of the one or more instrument. The one or more screenshots may be captured and transmitted to the remote technician substantially in real time. The processor executable code, when executed by the processor, may further cause the processor to convert the one or more captured screenshots into a video, and to transmit a fifth signal over the intranet network to the remote technician, the fifth signal indicative of the video. The video may be transmitted to the remote technician substantially in real time. The one or more instrument may be a point-of-care instrument, an analyzer, a medical instrument, a laboratory instrument in a laboratory setting, an industrial machine, an industrial device, or an industrial robot, and combinations thereof.

In yet another aspect, the inventive concepts disclosed herein are directed to a method comprising: (1) authenticating a user device and a user of the user device by a processor coupled to an intranet network; and (2) establishing communication between the user device and an instrument coupled with the intranet network subsequent to the authentication of the user device and the user.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals may refer to the same or similar elements for consistency. For purposes of clarity, not every component may be labeled in every drawing. Certain features and certain views of the figures may be shown exaggerated and not to scale or in schematic in the interest of clarity and conciseness. In the drawings:

FIG. 2 is a diagram of a screenshot showing an exemplary embodiment of a login screen of a handheld user device according to the inventive concepts disclosed herein.

FIG. 3 is a diagram of a screenshot showing an exemplary embodiment of a main menu screen of a handheld user device according to the inventive concepts disclosed herein.

FIG. 4 is a diagram of a screenshot showing an exemplary embodiment of an instrument list screen of a handheld user device according to the inventive concepts disclosed herein.

FIG. 5 is a diagram of a screenshot showing an exemplary embodiment of a device detail screen of a handheld user device according to the inventive concepts disclosed herein.

DETAILED DESCRIPTION

Figure 1:
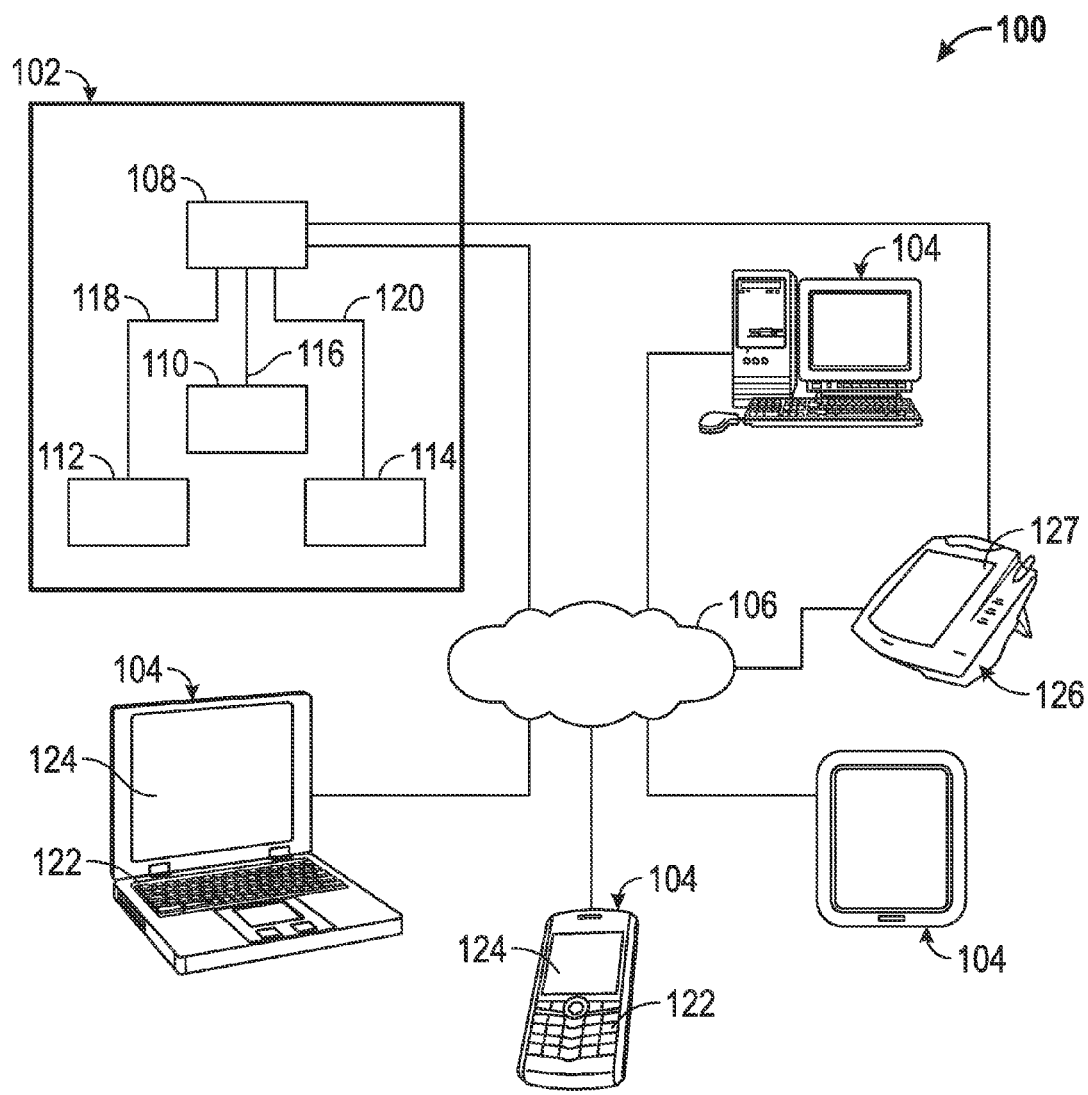
FIG. 1 is a diagram of an exemplary embodiment of a web-based data and instrument management and interface system according to the inventive concepts disclosed herein.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts disclosed herein may be practiced without these specific details. In other instances, well-known features have not been described in detail to avoid unnecessarily complicating the instant disclosure.

As used herein, the terms "web browser application," "web browser app," "web app," "web-based application," and variations thereof are intended to cover a web browser shortcut that may be initiated by a shortcut, icon, or other user-selectable interface feature on a user device having a web browser, that appears to a user as a native application on the user device, but is a web browser shortcut that causes the web browser running on the user device to communicate with a web server over a computer network and to present a web page, a web site, or other data to the user on the user device, for example, as a web page or substantially similarly to a native application running on the user device, and combinations thereof. Further, the terms "web browser application," "web browser app," "web app," "web-based application," and variations thereof may refer to a browser shortcut, bookmark, or similar user-selectable interface feature which may be selected or activated by the user from within a web browser after the user has previously launched the web browser or opened a web browser window, for example. Further, in some embodiments the terms "web browser application," "web browser app," "web app," "web-based application," and variations thereof may refer to a designated button or other similar mechanism provided on a user device which may cause a web browser on the user device to communicate with a web server over a computer network and to present a web page, a web site, or other data to the user on the user device, for example, as a web page or substantially similarly to a native application running on the user device, for example.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "data and instrument management and interface system," "data and instrument management and interface program," and variations thereof are intended to include a system or program that is configured to allow centralized management of one or more or multiple instruments/devices and operators to standardize procedures, facilitate compliance, and improve risk management. A data and instrument management and interface system or program may be implemented as any desired computer system, hardware, firmware, software, and/or processor executable code stored in a non-transitory computer memory, and combinations thereof, and may be at least partially or wholly network based, as will be appreciated by persons of ordinary skill in the art having the benefit of the instant disclosure. Further, a data and instrument management and interface system or program may function to limit access to trained and authorized users, remotely lock-out users or adjust access levels, electronically transmit patient and quality control data, generate customized reports eliminating manual data handling, standardize test protocols and drive quality control testing remotely, and combinations thereof, for example.

Finally, as used herein qualifiers such as "about," "approximately," and "substantially" are intended to signify that the item or value being qualified is not limited to the exact value or amount specified, but includes some slight variations or deviations therefrom, caused by measuring error or imprecision, manufacturing tolerances, stress exerted on various parts, wear and tear, and combinations thereof, for example.

The inventive concepts disclosed herein provide the ability to users to manage the data across one or more point of care medical instruments through a web-based handheld device application. Users would get the ease of use to be able to manage one or more devices or medical instruments within a hospital from anywhere within the hospital's wireless intranet range. In one exemplary embodiment, access to the one or more device or medical instrument is limited to the hospital's wireless intranet range such that the devices or medical instruments are not accessible by an internet connection from within or outside of the hospital.

Referring now to FIG. 1, an exemplary embodiment of a web-based data and instrument management and interface system 100 according to the inventive concepts disclosed herein may comprise one or more web server 102 hosted on an intranet network 106 and capable of interfacing and/or communicating with one or more user device 104 over the intranet network 106.

The one or more web server 102 may be implemented as any desired computer system and may form a host system or server, such as a website, and the intranet network 106 may be any desired intranet network (e.g., wired, wireless, or combinations thereof), a local area network, or a local wireless network, and combinations thereof, for example.

The one or more web server 102 may comprise one or more personal computers, mainframe computers, servers, web servers, local servers, intranet servers, and combinations thereof. In one embodiment, the one or more web server 102 may have a processors 108 capable of executing processor executable code, one or more non-transitory memory 110 capable of storing processor executable code, an input device 112, and an output device 114, all of which can be partially or completely network-based or cloud-based, and not necessarily located in a single physical location. The one or more web server 102 may be hosted on the intranet network 106, and/or may not be accessible over an external network such as the Internet in some exemplary embodiments of the inventive concepts disclosed herein.

The processor 108 can be implemented as a single processor 108 or multiple processors 108 working together to execute the logic described herein. Exemplary embodiments of the processor 108 may include a digital signal processor (DSP), a central processing unit (CPU), a field programmable gate array (FPGA), a microprocessor, a multi-core processor, and combinations thereof. The processor 108 is capable of communicating with the one or more memories 110 via a path 116 which can be implemented as a data bus, for example. The processor 108 is capable of communicating with the input device 112 and the output device 114 via paths 118 and 120 including one or more data busses, for example. The processor 108 may be further capable of interfacing and/or communicating with the one or more user device 104 via the intranet network 106, such as by exchanging electronic, digital and/or optical signals via one or more physical or virtual ports using any desired network protocol such as TCP/IP, for example. It is to be understood that in certain embodiments using more than one processor 108, multiple processors 108 may be located remotely from one another, located in the same location, or comprising a unitary multi-core processor (not shown). The processor 108 is capable of reading and/or executing processor executable code stored in the one or more memory 110 and/or of creating, manipulating, altering, and storing computer data structures into the one or more memory 110.

The one or more memory 110 may store a data and instrument management and interface program having processor executable code. The one or more memory 110 may be implemented as any conventional non-transitory memory, such as random access memory (RAM), a CD-ROM, a hard drive, a solid state drive, a flash drive, a memory card, a DVD-ROM, a floppy disk, an optical drive, and combinations thereof, for example. While the one or more memory 110 may be located in the same physical location as the web server 102, the one or more memory 110 may also be located remotely from the web server 102 and may communicate with the processor 108 via the network 106. Additionally, when more than one memory 110 is used, one or more memory 110 may be located in the same physical location as the web server 102, and one or more memory 110 may be located in a remote physical location from the web server 102. The physical location of the one or more memory 110 can be varied, and the one or more memory 110 may be implemented as a "cloud memory" i.e., one or more memory 110 which is partially, or completely based on or accessed using the intranet network 106, for example. Further, the one or more processor 108 may not communicate directly with the one or more memory 110, but may communicate with another processor 108 communicating with the one or more memory 110 over the intranet network 106, for example. In some exemplary embodiments, a first processor 108 may communicate with a second processor 108 executing processor executable code including a data and instrument management and interface program over the intranet network 106. The second processor 108 may be part of a computer station (not shown), or may be a part of a separate computer system or server configured to communicate with the web server 102 over the intranet network 106 or otherwise operably coupled with the web server 102, for example.

The input device 112 may pass data to the processor 108, and may be implemented as a keyboard, a mouse, a touchscreen, a camera, a cellular phone, a tablet, a smart phone, a PDA, a microphone, a network adapter, and combinations thereof, for example. The input device 112 may be located in the same physical location as the web server 102, or may be remotely located and/or partially or completely network-based.

The output device 114 passes information from the processor 108 to a user, such that the information can be perceived by the user. For example, the output device 114 can be implemented as a server, a computer monitor, a cell phone, a smartphone, a tablet, a speaker, a website, a personal digital assistant, a fax, a printer, a projector, a laptop monitor, and combinations thereof. The term "pass" as used herein may refer to either push technology, or to pull technology, and to combinations thereof. The output device 114 can be physically co-located with the web server 102, or can be located remotely from the web server 102, and may be partially or completely network based (e.g., a website). The output device 114 communicates with the processor 108. As used herein the term "user" is not limited to a human, and may comprise a human, a computer, a host system, a smart phone, a tablet, and combinations thereof, for example.

The intranet network 106 may be implemented as a wireless and/or wired intranet network 106, and may permit bi-directional communication of information and/or data between the web server 102 and/or one or more user device 104 located within the intranet network 106 or otherwise operably coupled with the intranet network 106, for example. In some exemplary embodiments, the intranet network 106 may have a wireless range that may be limited to a hospital, or other facility, for example, and may not allow access to the web server 102 to user devices 104 located outside the wireless range of the intranet network 106.

The intranet network 106 may interface with the web server 102 hosted on the intranet network 106, and with one or more user device 104 located within the wireless range of the intranet network 106 or otherwise operably coupled with the intranet network 106 in a variety of ways, such as by optical, wireless, wired, and/or electronic interfaces, and may use a plurality of network topographies and protocols, such as Ethernet, TCP/IP, circuit switched paths, and combinations thereof, for example. The intranet network 106 may use a variety of network protocols to permit bi-directional interface and communication of data and/or information between the web server 102 and the one or more user device 104 located within the wireless range of the intranet network 106 or otherwise operably coupled with the intranet network 106. The intranet network 106 may be accessible only to user devices 104 located within the wireless range of the network 106 or otherwise operably coupled with the intranet network 106, and may be secured using any desired secured networking protocol, such as a gateway server, a firewall, data encryption, public or private key cryptography infrastructure, secure socket layer protocol, hypertext transfer protocol secure, a virtual private network, a tunnel, secure shell, and any combinations thereof, for example. In some exemplary embodiments, a separate computer system or server running or executing a data and instrument management and interface system may be operably coupled with the intranet network 106 so that the separate computer system of server may communicate with the web server 102, the one or more medical instrument 126, and the user device 104 over the intranet network 106, for example.

The one or more user device 104 may be connected or otherwise operably coupled with the intranet network 106 and can be implemented as any desired handheld or portable wireless user device, such as a personal computer, a smartphone, a tablet, an e-book reader, a laptop computer, a designated handheld reader device, a wireless network-capable handheld device, a digital video recorder, a personal digital assistant, and combinations thereof, for example. In an exemplary embodiment, the user device 104 may comprise an input device 122, an output device 124, a processor (not shown) capable of wirelessly interfacing with the computer network 106 when the user device 104 is within the wireless range of the intranet network 106, one or more non-transient memory storing processor executable code or software applications, and a web browser or web application running on the user device 104 and capable of accessing a website and/or communicating information and/or data with a web server such as the web server 102 over a network, such as the intranet network 106.

In some exemplary embodiments, the user device 104 may be implemented as a desktop computer or computer station or terminal, and may be operably coupled with the intranet network 106 via a wireless or via a wired connection, as will be appreciated by a person of ordinary skill in the art having the benefit of the instant disclosure.

The input device 122 may be implemented as any desired input device, such as a keyboard, a touchscreen, a stylus, a mouse, a trackball, and combinations thereof, for example.

The output device 124 may be implemented as any desired output device 124 configured to show, display, or otherwise present information in a form perceivable by a user, such as a screen, a touchscreen, a monitor, a printer, a speaker, and combinations thereof, for example.

One or more medical instrument 126 having a screen 127 may be operatively coupled with the intranet network 106 and may optionally be coupled with the web server 102 via the intranet network 106 (e.g., via a wired and/or wireless connection), may be operably coupled with the web server 102 (e.g., directly or via the intranet network 106), or may be operably coupled with a separate server or computer system (not shown) running a data and instrument management and interface system as described herein, for example. The one or more medical instrument 126 may be a diagnostic instrument, such as an analyzer, or a point of care instrument, for example.

The screen 127 may be configured to display information, such as text, images, or videos, for example, in a form perceivable by a user. The screen 127 may be a touch screen, a computer monitor, an LCD display, an LED display, and combinations thereof, for example.

The data and instrument management and interface program may include processor executable code written in any suitable programming language, such as C++, for example. The data and instrument management and interface program may be implemented as processor executable code, software, firmware, or a combination of software and firmware, for example, and may be stored in the one or more memory 110. The web server 102 may access and execute the processor executable code to connect one or more user device 104 to one or more medical instrument 126, for example.

In some exemplary embodiments, the web server 102 may communicate (e.g., bi-directionally exchange data and/or processor executable code) with a separate computer system (not shown) or computer server (not shown) operably coupled with the intranet network 106 and executing a data and instrument management and interface program over the intranet network 106, as will be appreciated by a person of ordinary skill in the art having the benefit of the instant disclosure. In some exemplary embodiments, the web server 102 may execute or run a data and instrument management and interface program including processor executable code, such as via accessing and executing processor executable code stored in the memory 110.

Referring now to FIG. 2 shown therein is an exemplary embodiment of a login screen 130 that may be displayed to a user of a web browser running on the user device 104, such as via the output device 124, for example. As can be seen in FIG. 2, before a user is allowed access to the web server 102, the user may be provided with a login screen 130 prompting the user to provide credentials, such as a username and a password, in one or more input or text boxes, for example. As part of the login process, the web server 102 may determine if the user device 104 is within the wireless range of the intranet network 106, if the user device 104 is authenticated on the intranet network 106, or if the user device 104 is outside the wireless range of the intranet network 106 and is attempting to access the web server 102 from outside the wireless range of the intranet network 106, for example.

If the user device 104 is not within the wireless range of the intranet network 106 and/or if the user device 104 is not authenticated on the intranet network 106, the web server 102 may not allow the user device 104 to access the one or more medical instrument. If the user device 104 is within the wireless range of the intranet network 106, or if the user device 104 is otherwise authenticated on the intranet network 106, the web server 102 may proceed with authenticating a user of the user device 104, for example.

The user may use the input device 122 to enter any requested credentials, such as by typing on a keyboard, or touching a touchscreen, for example to enter such credentials in a text box. In some exemplary embodiments, biometric credentials and associated input devices (not shown) such as a fingerprint reader or a camera with facial recognition may be used to authenticate the user. A user-selectable log on interface (not referenced) may be selected by the user to transmit the entered credentials to the web server 102, for example. The credentials provided by the user may be transmitted over the intranet network 106 to the web server 102 such as via one or more wireless signal transmitted between the web browser running on the user device 104 and the web server 102, so that the user may be logged in and/or authenticated by the web server 102, for example.

An optional "remember me" user-selectable interface such as a checkbox (not referenced) may be provided in some exemplary embodiments of the login screen 130, and may function to remember the user, such as by placing a browser cookie on the web browser running on the user device 104, as will be appreciated by persons of ordinary skill in the art having the benefit of the instant disclosure.

Referring now to FIG. 3, once the user of the web browser running on the user device 104 has been authenticated and/or otherwise logged on or logged in to the web server 102, the user may be presented with a main menu screen 132, and may be allowed to select one or more user-selectable interface (e.g., via the input device 122). In the exemplary embodiment shown in FIG. 3, the user may select a first user-selectable interface 134 that takes the user to a screen listing one or more medical instruments 126 or devices which the user is authorized to view, operate, and/or control, for example.

A second user-selectable interface 136 may allow the user to manage medical instrument operators, such as by assigning a new operator to one or more medical instrument 126, or by removing an operator from one or more medical instrument 126, for example, provided that the user is authorized to manage operators of the one or more medical instrument 126 operators by virtue of being a supervisor or an administrator, for example.

A third user-selectable interface 138 may allow the user to view events and event logs from one or more medical instruments 126 for which the user is an operator or an administrator, for example.

A fourth user-selectable interface 140 may allow the user to request a remote connection with one or more medical instrument 126 from the web server 102, for example.

A fifth user-selectable interface 142 may allow the user to log off the web server 102, for example.

An optional back interface (not referenced) may be provided to allow the user to navigate to one or more previous screens, as will be appreciated by persons of ordinary skill in the art having the benefit of the instant disclosure.

Referring now to FIG. 4, shown therein is a screenshot of a screen 144 showing a list of one or more medical instruments 126 that the user is authorized to view, or for which the user is an operator. The user may be presented with such screen 144 by the web server 102 in response to the user selecting the first user-selectable interface 134 described above. The user may view a list of one or more medical instruments 126, which list may be organized in any desired manner, such as alphabetically, by medical instrument 126 location, by medical instrument 126 type, by medical instrument 126 trouble codes or alerts, or as selected by the user, and combinations thereof, for example. While two medical instruments 126 are shown in FIG. 4, the screen 144 may include one, two, or more than two medical instruments 126, and the user may scroll up or down the screen 144 when more medical instruments 126 are shown than can fit on a single screen 144, for example. The user may be able to select one or more of the medical instruments 126 listed on the screen 144, and may be taken to a screen with more details or data for that particular medical instrument 126 as will be described below, for example. The screen 144 may provide an alert to the user in the event one or more medical instrument 126 is experiencing a malfunction, is low on reagents, is due for a quality control check, or otherwise needs the user's attention. The alert may be a visual alert (e.g., a flashing notification light, screen, a certain color of a user-selectable interface or graphical element on the screen 144), an audible alert (e.g., a sound made by the user device 104), a tactile alert (e.g., vibration of the user device 104), and combinations thereof, for example. For example, the alert may be communicated to the user of the web browser running on the user device 104 in any manner in which the web browser is configured to alert the user of the user device 104, which may vary between user devices 104 as will be appreciated by persons of ordinary skill in the art having the benefit of the instant disclosure.

An optional back interface (not referenced) may be provided to allow the user to navigate to one or more previous screens, as will be appreciated by persons of ordinary skill in the art having the benefit of the instant disclosure.

Referring now to FIG. 5, shown therein is a screenshot of an exemplary device details screen 146 according to the inventive concepts disclosed herein. The device detail screen 146 may display detailed information or data for a user-selected medical instrument 126 from the screen 144, for example. The information or data for the medical instrument 126 may be obtained by the web server 102 from the medical instrument 126 in response to the user selecting the medical instrument 126 on the screen 144 as described above, for example, or in response to the user logging on into the web server 102 where the user is authorized to view information or data for the medical instrument 126, for example. In some exemplary embodiments, data from the one or more medical instrument 126 may be obtained by the web server 102 from a separate computer system (not shown) coupled with the intranet network 106, the web server 102, and the one or more medical instrument 126.

The information or data for the medical instrument 126 may include any desired information or data about the medical instrument 126 or from the medical instrument 126, such as medical instrument 126 make, model, model type, name, location, type, software version, connection status, last patient to use the medical instrument 126, last quality control check performed on the medical instrument 126, one or more images or screenshots of the screen 127 of the medical instrument 126, test results, analysis results, event logs, patient lists, reagent levels, quality control information, current status, patient list, operator list, location, and any other desired information, and combinations thereof, for example. A stock image or an actual image of the medical instrument 126 may optionally be displayed on the screen 146, for example.

The screen 146 may include a user-selectable device link interface 148 allowing a user to request a remote connection to the medical instrument 126 from the web server 102, for example, by the web browser running on the user device 104 transmitting a signal to the web server 102 over the intranet network 106. In response to receiving a signal indicative of the user selecting, or activating the interface 148, the web server 102 may establish a remote connection between the medical instrument 126 and the user device 104, for example, by transmitting one or more wireless signals to the user device 104 or by transmitting one or more signals to the medical instrument 126 or by receiving one or more wireless signals from the user device 104 or from the instrument over the intranet network 106. As part of the remote connection, the user may view one or more images, screenshots, or video of the screen 127 of the medical instrument 126 on the user device 104, such as via providing the one or more images, screenshots, or video to the user device 104 by the web server 102 via one or more wireless signals transmitted over the intranet network 106, for example. In some exemplary embodiments, as part of the remote connection, the user may have access to some or all functions, settings, or options of the medical instrument 126, such as troubleshooting problems, editing settings, running quality control, or accessing test results, operator lists, patient lists, reagent levels, event logs and combinations thereof. As will be appreciated by persons of ordinary skill in the art, the user may have access to some or all medical instrument 126 functions, information, and/or features through the remote connection via the user device 104, except for running a sample through the medical instrument 126, for example.

The screen 146 may also include a user-selectable video log interface 150 allowing the user to send a request or a command (e.g., via a wireless signal transmitted by the user device 104 to the web server 102 over the intranet network 106) to the web server 102 to initiate capture of screenshots of the screen 127 of the medical instrument 126, for example. In response to the user selecting, or otherwise activating the interface 150, the web server 102 may initiate capture of one or more screenshots of the screen 127 of the medical instrument 126, for example, and may store such captured screenshots in the one or more memory 110, and/or transmit such captured screenshots to the user device 104, or to another computer system via the intranet network 106. In some exemplary embodiments, the web server 102 may convert the one or more captured screenshots into video, and store such video in the one or more memory 110, or transmit such video to one or more user device 104 or to another computer system via the intranet network 106, or via a separate computer network such as another intranet network 106 or the Internet, and combinations thereof.

For example, to initiate the capture of screenshots, the web server 102 may receive a first signal over the intranet network 106 indicative of a command to initiate capture of one or more screenshots of the screen 127 of the one or more medical instrument 126 from the web browser. The web server 102 may receive a second signal from the one or more medical instrument 126, the second signal indicative of one or more screenshots of the screen 127 of the one or more medical instrument 126. The web server 102 may capture one or more screenshots of the screen 127 of the one or more medical instrument 126 and may transmit a third signal over the network 106 to the web browser indicative of the one or more captured screenshots. The web server 102 may transmit a fourth signal over the intranet network 106 (or via a separate computer network) to a remote technician and/or to the handheld user device 104, the fourth signal indicative of the one or more captured screenshots of the one or more medical instrument 126, for example. Optionally, web server 102 may convert the one or more captured screenshots into a video, and may transmit a fifth signal over the network 106 (or via a separate computer network such as another intranet network 106 or the Internet) to the remote technician and/or to the handheld user device 104, the fifth signal indicative of the video.

This web server 102 may capture or transmit the one or more screenshots substantially in real time as the one or more screenshots of the screen 127 are displayed on screen 127, so that the technician may observe and troubleshoot an ongoing issue with the medical instrument 126, for example. However, in some exemplary embodiments, the capturing of the screenshots may not be carried out in real time, and the screenshots and/or the video may be stored by the web server 102 in the one or more memory 110, and may be sent to a local or remote technician or support staff at a later time, as will be readily appreciated by persons of ordinary skill in the art having the benefit of the instant disclosure.

An optional back interface (not referenced) may be provided to allow the user to navigate to one or more previous screens, as will be appreciated by persons of ordinary skill in the art having the benefit of the instant disclosure.

Figure 6:
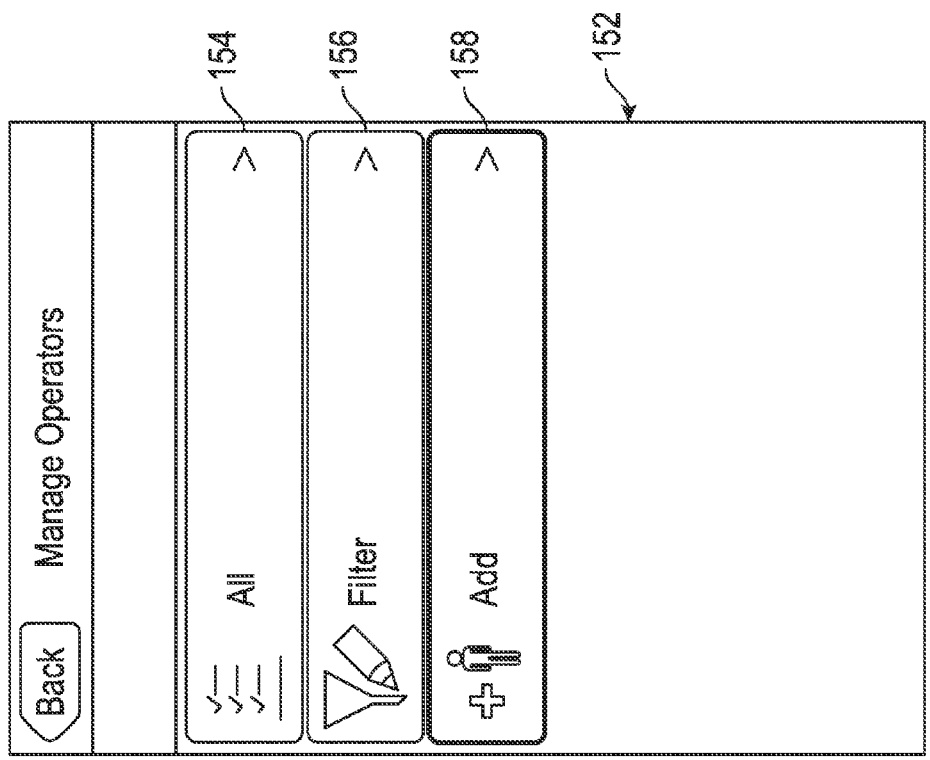
FIG. 6 is a diagram of a screenshot showing an exemplary embodiment of a manage operators menu screen of a handheld user device according to the inventive concepts disclosed herein.

Referring now to FIG. 6, if the user has administrative privileges for one or more medical instrument 126, the user may be presented with a screen 152, allowing the user to manage operators for the medical instrument 126. For example, the user may be provided with a user-selectable interface 154 allowing the user to view all operators for one or more medical instrument 126, for example. The user may also be provided with a user-selectable interface 156 allowing the user to filter operators of one or more medical instrument 126 based on any desired criteria, such as by medical instrument 126, name, operator name, medical instrument 126 location, medical instrument 126 model type, and combinations thereof, for example. The user may also be provided with a user-selectable interface 158 allowing the user to add one or more operators for one or more medical instrument 126, for example.

An optional back interface (not referenced) may be provided to allow the user to navigate to one or more previous screens, as will be appreciated by persons of ordinary skill in the art having the benefit of the instant disclosure.

Figure 7:
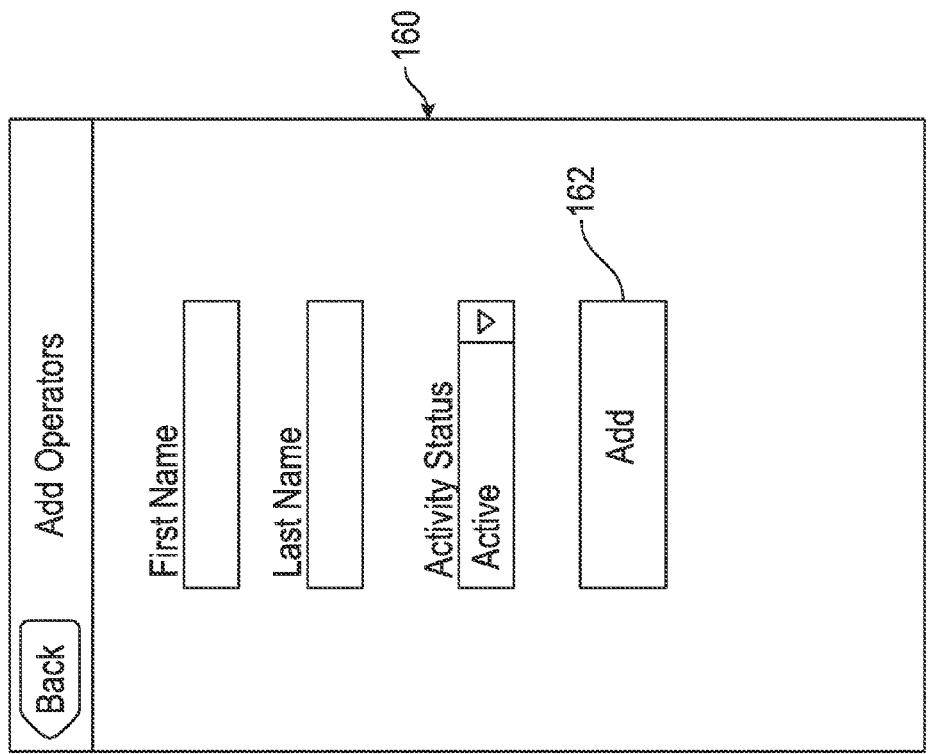
FIG. 7 is a diagram of a screenshot showing an exemplary embodiment of an add operator screen of a handheld user device according to the inventive concepts disclosed herein.

Referring now to FIG. 7, if the user selects, or otherwise activates the interface 158, the user may be presented with a screen 160, allowing the user to input the first and last name, and the activity status of an operator the user wishes to add for one or more medical instrument 126 (e.g., active or inactive). As will be appreciated by persons of ordinary skill in the art, the operators may be pre-registered with the web server 102, and a list, or data table, of all registered operators may be maintained by the web server 102, or by another computer system of computer station with which the web server 102 can communicate bi-directionally over the intranet network 106, for example. Once the user has entered the name and activity status of a desired operator (e.g., in a text box or a drop down selection box), the user may select, or otherwise activate a user-selectable interface 162 to add the operator to a desired medical instrument 126, or to more than one medical instrument 126, for example. As will be readily appreciated by persons of ordinary skill in the art, operators may be removed by the user in a similar fashion.

An optional back interface (not referenced) may be provided to allow the user to navigate to one or more previous screens, as will be appreciated by persons of ordinary skill in the art having the benefit of the instant disclosure.

Figure 8:
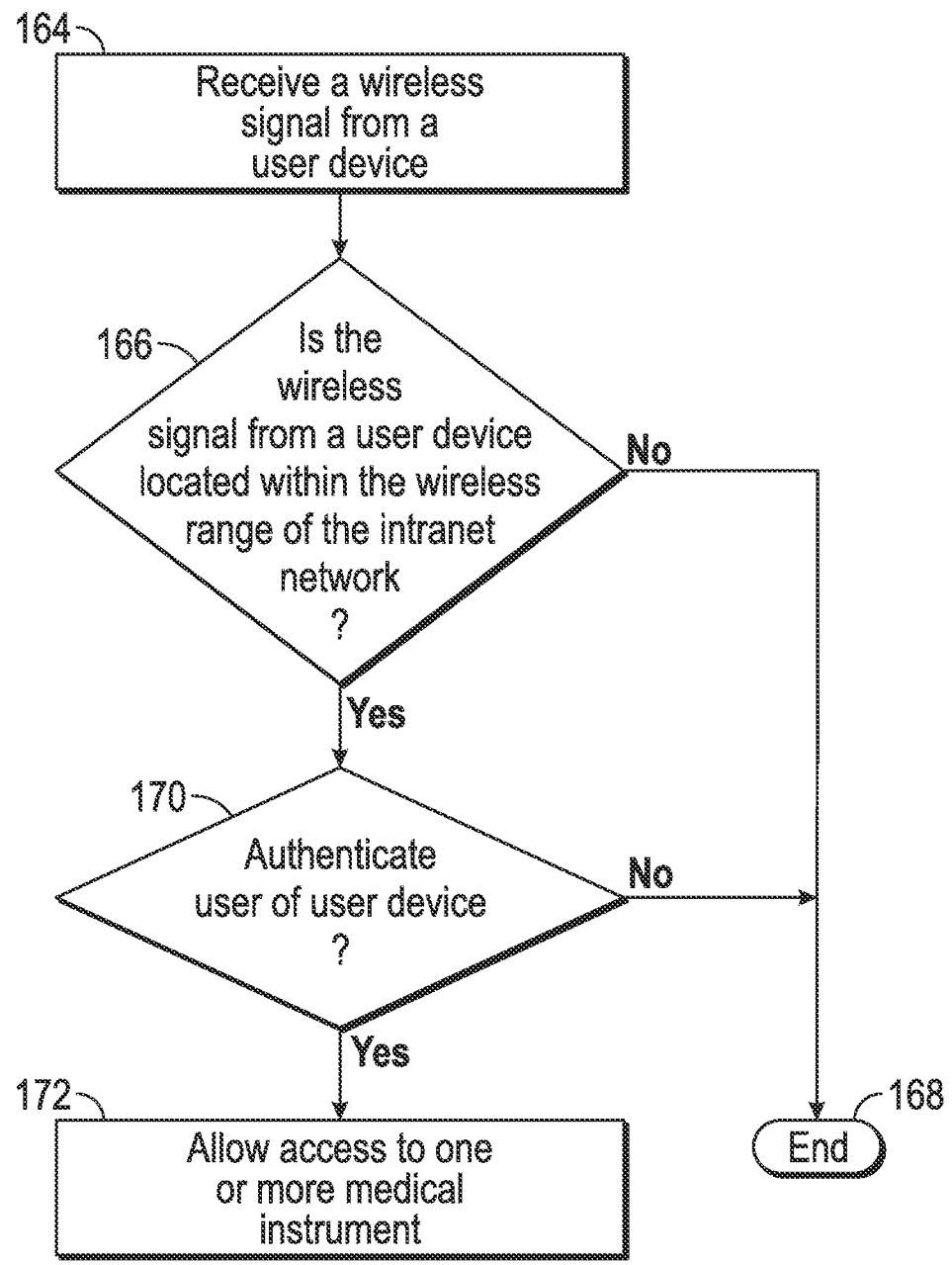
FIG. 8 is a diagram showing an exemplary embodiment of an authentication decision process for a web-based data and instrument management and interface system according to the inventive concepts disclosed herein.

Referring now to FIG. 8, in some exemplary embodiments of the inventive concepts disclosed herein, a system 100 may authenticate a user of a web browser running on a user device 104 as follows. The web server 102 may receive a signal from the web browser running on the user device 104 over the intranet network 106 as shown in box 164, the signal may be received via the intranet network 106 and may be a wireless signal. In response to receiving the signal, the web server 102 may determine if the signal is from a user device 104 located within the wireless range of the intranet network 106, or from a device authenticated on the intranet network 106, or otherwise operably coupled with the intranet network 106 in a decision step 166. If the signal is not from a user device 104 located within the wireless range of the intranet network 106 or otherwise authenticated on the intranet network 106 or operably coupled with the intranet network 106, the web server 102 may move to an end step 168.

In some exemplary embodiments, the hospital's IT department may maintain a list of one or more authorized user device 104, and a user device 104 may be authenticated by the intranet network 106 prior to requesting access to the web server 102 (e.g., via a separate authentication server or process), as will be readily recognized by persons of ordinary skill in the art having the benefit of the instant disclosure. Further, in some exemplary embodiments a user device 104 may request access to the web server 102 from the Internet, such as via a Virtual Private Network, or via any suitable secured or unsecured protocol. The user device 104, or a user of the web browser running on the user device 104 may be authenticated in any suitable manner, or by using any desired secured or unsecured authentication protocol, which may be determined by a hospital's IT department, by the intranet network 106 authentication and/or security policies, or by the web server 102, and combinations thereof, for example. A list of one or more predetermined user devices 104 may be maintained by the web server 102 or by another server coupled with the intranet network 106, and the web server 102 may determine if the user device 104 is included in the list of predetermined user devices 104 prior to authenticating the user device, for example.

If the signal is from a user device 104 located within the wireless range of the intranet network 106 or otherwise operably coupled with the intranet network 106, the web server 102 may authenticate a user of the web browser running on the user device 104 in a decision step 170, or may obtain such authentication from the intranet network 106, for example. In some exemplary embodiments, the web server 102 may assume that a user of the web browser running on the user device 104 from within the wireless range of the intranet network 106 is authenticated by the intranet network 106, for example, and proceed accordingly by treating such user device 104 as successfully authenticated and may proceed with authenticating a user of the user device 104 as described above. If the user or the user device 104 is not successfully authenticated, the web server 102 may proceed to the end step 168. If the user of the web browser running on the user device 104 is successfully authenticated, the web server 102 may move to a step 172 and may allow access to the data and instrument management and interface system 100 and/or to the one or more medical instrument 126 to the user of the web browser running on the user device 104 as described above, for example.

With the inventive concepts disclosed herein, users no longer need to be physically near the computer station where the data and instrument management and interface software is installed. Users could go to any computer terminal in the hospital or use any handheld or mobile device having a web browser to access the data and instrument management and interface system 100.

In some exemplary embodiments of the inventive concepts disclosed herein, one or more features of one or more medical instrument 126 could be made available to the wireless handheld user device 104 via the web server 102. For example, when coupled with a data and instrument management and interface program such as a RAPIDComm® system, the ability to request and download configuration settings to the CLINITEK Status® Connect System allows a point of care coordinator to configure one medical instrument 126 and then, at the RAPIDComm® application, to instantly "copy and paste" the configuration settings to all medical instruments 126 or a subset of the medical instruments 126. While the POCT1-A2 protocol relies upon a robust standard network protocol, loss of connection can occur through network outages or when operators power-off analyzers or medical instruments 126. The RAPIDComm® v3.0 system may constantly monitor the status of all analyzer or medical instrument 126 connections and may provide a warning indicator regardless of the RAPIDComm® function being accessed. The RAPIDComm® v3.0 application also offers many new features for Siemens blood gas instrument users, including audit trail reporting, analyzer reagent and control material reports, and the ability to view and navigate RAPIDLab 1200 and RAPIDPoint 400, 405, and 500 blood gas analyzer screens from any location where there is a RAPIDComm client or from a wireless device via the web application. The latter feature allows a point of care coordinator to perform any task (other than running a patient sample) wirelessly and/or from a remote location, greatly assisting in diagnosing analyzer or medical instrument 126 and operator problems. The web application's easy-to-use navigational design, coupled with the ability to create separate views of the application for each user, allows users to see only data from, and control the configuration of, analyzers or medical instruments 126 in their purview, keeping the application as simple as possible. The RAPIDComm® v3.0 data management system allows users to oversee remote blood gas and urinalysis systems or medical instruments 126, operator proficiency, and compliance and quality control management without spending hours traveling throughout their healthcare institution or network.

It is to be understood that while the inventive concepts disclosed herein have been described in detail in connection with medical instruments such as point of care instruments, analyzers, and diagnostic instruments used in a clinical or hospital settings, the inventive concepts disclosed herein are expressly not limited to such medical instruments, or to such hospital settings or applications. For example, in some embodiments, a web-based data and instrument management and interface system 100 may be implemented in a laboratory setting, in an industrial setting, or in any other settings where it would be advantageous to remotely monitor or access one or more instruments, devices, machines, or processes over a web-based interface.

As an example, laboratory instruments and/or equipment in a laboratory setting (off-site or on-site) may be accessed using a web-based data and instrument management and interface system 100 as described herein. Further, as another example, one or more industrial machines, devices, or robots, may be remotely accessed via a web-based data and instrument management and interface system 100, such as from a control room or command center. The contemplated industrial applications of the inventive concepts disclosed herein are numerous, and may include oilfield equipment and processes, mining equipment, chemical plant equipment, nuclear power plant equipment and processes, metallurgical equipment and processes, food processing equipment and processes, and any other desired industrial, clinical, or household application, as will be appreciated by a person of ordinary skill in the art having the benefit of the instant disclosure, for example.

As will be appreciated by persons of ordinary skill in the art any desired data and instrument management and interface system software may be implemented with exemplary embodiments of the inventive concepts disclosed herein.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

The invention claimed is:

1. A data and instrument management and interface system, comprising:
　a web server hosted on an intranet network within at least one of a clinical or hospital setting and having a wireless range, the web server having a processor capable of executing processor executable code, and one or more non-transitory computer memory operably coupled with the processor and storing processor executable code;
　wherein the web server is configured to communicate over the intranet network with a web browser running on a handheld user device located within the wireless range of the intranet network and to communicate with one or more medical instrument capable of running a patient sample coupled with the web server and within the at least one of the clinical or hospital setting, and wherein the processor executable code, when executed by the processor, causes the processor to:
　　receive a first wireless signal over the intranet network, the first wireless signal transmitted by the web browser running on the handheld user device from within the wireless range of the intranet network and indicative of a request from a point of care coordinator to configure configuration settings of the medical instrument and modify the authorization status of at least an operator having a configuration setting of the one or more medical instrument;
　　authenticate that the handheld user device is located within the wireless range of the intranet network, by determining if the user device is authenticated on the intranet network, or is attempting to access the web server from outside of the wireless range of the intranet network;
　　authenticate that the point of care coordinator of the web browser running on the handheld user device has administrative privileges for the one or more medical instrument by presenting a login screen to the web browser, receiving credentials entered into the login screen, and authenticating the credentials;
　　transmit a second wireless signal over the intranet network to the web browser running on the handheld user device responsive to the handheld user device, the point of care coordinator being authenticated, and the received first wireless signal, the second wireless signal indicative of the modified authorization status of the operator of the one or more medical instrument;
　　establish a remote connection between the handheld user device and the one or more medical instruments in which the point of care coordinator is prevented from running a sample through the one or more medical instrument via the remote connection; and
　　transmit a third signal over the intranet network to the one or more medical instrument responsive to authenticating the handheld user device, authenticating the point of care coordinator, and the received first signal, the third signal indicative of the modified authorization status of the operator and the configuration settings of the one or more medical instrument wherein operators lacking a supervisory or an administrator privilege are unable to change their own configuration setting.

2. The system of claim 1, wherein the handheld user device is authenticated by accessing a list of one or more predetermined handheld user devices.

3. The system of claim 1, wherein the first signal is a request to one of add the operator to a list of authorized users of the one or more medical instrument or remove the operator from the list of authorized users of the one or more medical instrument.

4. The system of claim 1, wherein the second signal is sent via a user-selectable interface displayed on the handheld user device.

5. The system of claim 1, wherein the one or more medical instrument is a point-of-care instrument.

6. The system of claim 1, wherein the one or more medical instrument is a laboratory instrument in a laboratory setting.

7. A data and instrument management and interface system, comprising:
　a web server hosted on an intranet network, the web server having a processor capable of executing processor executable code, and one or more non-transitory computer memory operably coupled with the processor and storing processor executable code;
　wherein the web server is configured to communicate over the intranet network with a web browser running on a handheld user device coupled with the intranet network, and to communicate with one or more medical instrument capable of running a patient sample, having a screen and being coupled with the web server, and wherein the processor executable code, when executed by the processor, causes the processor to:
　　receive a first signal over the intranet network indicative of a command to initiate capture of one or more screenshots of the screen of the one or more medical instrument from the web browser running on the handheld user device;
　　authenticate the handheld user device by determining if the handheld user device is authenticated on the intranet network, or is attempting to access the web server from outside of the wireless range of the intranet network;
　　authenticate a user of the web browser running on the handheld user device, by presenting a login screen to the web browser, receiving credentials entered into the login screen, and authenticating the credentials;
　　establish a remote connection between the handheld user device and the one or more medical instruments in which the point of care coordinator is prevented from running a sample through the medical instrument via the remote connection;

receive a second signal from the one or more medical instrument, the second signal indicative of one or more screenshots of the screen of the one or more medical instrument;

store the one or more screenshots in the one or more non-transitory computer memory; and transmit a third signal over the intranet network to a computer system, the computer system being different than the handheld user device, the third signal containing the one or more captured screen shots.

8. The system of claim 7, wherein the computer system is operated by a remote technician.

9. The system of claim 8, wherein the one or more screenshots are not transmitted to the remote technician substantially in real time.

10. The system of claim 8, wherein the processor executable code, when executed by the processor, further causes the processor to convert the one or more captured screenshots into a video, and to transmit a fourth signal over the intranet network to the remote technician, the fourth signal indicative of the video.

11. The system of claim 10, wherein the video is not transmitted to the remote technician substantially in real time.

12. The system of claim 7, wherein the one or more medical instrument is a point-of-care instrument.

13. The system of claim 7, wherein the one or more medical instrument is a laboratory instrument in a laboratory setting.

* * * * *